United States Patent [19]

Blackburn et al.

[11] Patent Number: 5,031,469

[45] Date of Patent: Jul. 16, 1991

[54] FLUID SAMPLER

[76] Inventors: Robert E. Blackburn, 843 E. Washington Ave., Galesburg, Ill. 61401; Michael J. Blackburn, 505 E. Washington St., Morris, Ill. 60450; Sherry Blackburn, 843 E. Washington Ave., Galesburg, Ill. 61401; Lee A. Blackburn, 505 Washington St., Morris, Ill. 60450

[21] Appl. No.: 470,740

[22] Filed: Jan. 26, 1990

Related U.S. Application Data

[63] Continuation-in-part of Ser. No. 278,282, Nov. 30, 1988, abandoned.

[51] Int. Cl.⁵ .............................................. G01N 1/12
[52] U.S. Cl. .................................................. 73/864.63
[58] Field of Search ........... 73/864.51, 864.63–864.67, 73/864.91, 291, 298, 323

[56] References Cited

U.S. PATENT DOCUMENTS

| | | | |
|---|---|---|---|
| 1,210,487 | 1/1917 | Kaul | 73/864.63 |
| 2,040,701 | 5/1936 | Marsden | 73/864.63 |
| 3,955,423 | 5/1976 | Ohringer | 73/863.23 |
| 4,594,905 | 6/1986 | Roberts | 73/864.63 |
| 4,831,018 | 5/1989 | Kirsh et al. | 604/81 |
| 4,877,578 | 10/1989 | Zetlmeisl et al. | 208/47 |

FOREIGN PATENT DOCUMENTS

0046450  1/1889  Fed. Rep. of Germany ... 73/864.63

Primary Examiner—Robert Raevis
Attorney, Agent, or Firm—Sixbey, Friedman, Leedom & Ferguson

[57] ABSTRACT

A fluid sampling device includes a tube, one end of which is adapted to be placed into a fluid medium. An actuator on the opposite end moves a rod along the longitudinal axis of the tube to bring a stopper into and out of sealing engagement with the fluid receiving end of the tube. With the fluid receiving end open, it is placed beneath the level of the fluid. The pressure of the fluid causes fluid to enter the tube to the level of the surrounding fluid. Then the stopper is closed, thus sealing the fluid sample within the tube, so that the sample may be removed. A stopper for sealing the upper end of the tube may also be provided, with the actuator moving both the upper and lower stoppers. The tube is formed of polypropylene extruded to 0.050 inches ±0.005 inches and the stopper is formed of neoprene coated with polytetrafluoroethylene.

24 Claims, 3 Drawing Sheets

FLUID SAMPLER

This Application is a continuation-in-part of application Ser. No. 07/278,282 filed Nov. 30, 1988, now abandoned.

TECHNICAL FIELD

This invention relates generally to fluid sampling devices, and more particularly to a device for sampling fluid in a container.

BACKGROUND OF THE INVENTION

It is often desirable to obtain a sample of fluid which is held in a container or the like. Fluid samples are usually subjected to tests to determine the contents of the sample. Particularly in the field of work vehicles, fluid samples are taken at regular intervals because the sampling process is generally less expensive than changing the fluid. Many types of fluid, such as hydraulic fluid, engine oil, and transmission fluid, are commonly sampled so that the fluid may be tested for contaminates which result from vehicle operation and the operating environment. When the contaminates reach an undesirable level, the contaminated fluid is changed. Moreover, contaminates in fluid samples may also give an early indication of a component wear or failure. Therefore, the samples alert service personnel so that major failures or unexpected downtime are avoided.

Since some samples contain potentially hazardous constituents, it is advantageous to use a fluid sampling device which minimizes the risk of spilling the fluid sample on the sampling personnel or the surrounding area. Sampling devices have progressed so that they are partially or fully sealed to reduce spillage. Preferably, the material of the sampling device is inert with respect to the fluid and relatively unbreakable. Sampling devices should also be easy to use, inexpensive to manufacture, and adaptable to containers and openings of various designs.

Previous sampling devices have attempted to embody the above-mentioned attributes with varying degrees of success. U.S. Pat. No. 4,580,454, issued Apr. 8, 1986 to Deja, discloses a sampling tube, one end of which is inserted into a fluid so that a fluid sample enters the tube by displacing a portion of the air in the tube. A rod, having a handle on one end and a stopper on the other end, extends the length of the tube. When the handle is pulled upwardly, the stopper moves into contact with the bottom of the tube to retain the fluid sample within the tube. The handle is then pivoted into a locking position to prevent the stopper from dislodging from the end of the tube. A valve within the tube seals an upper portion of the tube when the stopper seals the bottom of the tube. One drawback of this device is that it needs to be manufactured to strict tolerances to insure proper operation for the valves as they are moved and locked by the handle. Moreover, there is no provision for adapting the device to sample fluid from a container which is deeper than the length of the tube or which has an opening smaller than the diameter of the tube.

In addition, sampling devices have not heretofore been available in which a suitable material is utilized such that the sampler is chemically resistant to the samples, inexpensive, relatively unbreakable and allows for visual inspection through the sampling device. For example, the use of glass samplers involves a risk that the sampler will break as the sample is obtained. Other materials such as PVC, polycarbonate, and polystyrene and polyolefins are adversely affected by many chemicals and/or do not provide sufficient visibility of the sample.

A lingering, unsolved problem with Coliwasa samplers is primarily a material problem, for a truly suitable material for forming a sampler has previously not been found. Coliwasas are used to sample hazardous waste material where one encounters the need to sample acids, caustics, aromatic hydrocarbons, aliphatic hydrocarbons, chlorinated hydrocarbons, ketones, alcohols, esters, etc. A sampler for the full variety of chemical substances known to man, must as top priority, be sufficiently chemically resistant to ensure the personal safety of those sampling the hazardous chemical. It must similarly be breakage-resistant and transparent enough to permit visual evaluation of the sample obtained.

Heretofore only two materials for sampler construction have been found which are suitable for nearly or all the chemicals likely to be encountered; Teflon and glass. However, glass breaks, and Teflon is both expensive and opaque. Samplers constructed of metal are attacked by acids and caustics and are non-see through; samplers of PVC are attacked by organic materials and petroleum products. Polycarbonate, polystyrene, ABS, cellulose acetate butyrate, nylon, etc. are all effected substantially by many chemicals.

Polyolefins (high density polyethylene and polypropylene) are generally cost-competitive and have good chemical resistance. The disadvantage of polyolefins is that they are translucent, not transparent. The functional requirement that the sample be visibly inspected right after sampling was not achievable, and copolymers such as those used to achieve clear polypropylene yield a flexible material—(not rigid). Consequently, polyolefins have been rejected as a suitable material for sampler construction.

In known devices it is often necessary to transfer the sample to a jar or other container for visual inspection or transportation. This makes the process more cumbersome since additional containers must be carried. In addition, clean-up is more time consuming since additional containers must be cleaned. The possibility that the sample will be spilled, or impurities introduced is also increased where it is necessary to transfer the sample into a separate container.

Suitable stoppers which are both pliable and chemically resistant have also been unavailable. For example, neoprene has been found unsuitable as a stopper material since it is not resistant to ketone, chlorinated solvents. Rubber and silicone are also unacceptable since although pliable, they are not chemically resistant to certain solvents. Although polytetrafluoroethylene (marketed by DuPont under the trademark Teflon) exhibits suitable chemical resistance, it is not pliable enough to ensure a reliable seal.

The present invention is directed to overcoming one or more of the problems as set forth above.

SUMMARY OF THE INVENTION

It is the primary object of the present invention to provide a fluid sampling device which is easy to use and manufacture.

It is an important object of the present invention to provide a fluid sampling device which fits into large fluid containers.

It is another object of the present invention to provide a fluid sampling device which can be adapted to fit into a variety of containers.

It is a further object of the invention to provide a fluid sampling device which is easily adaptable to various sampling needs and which is easy to disassemble for cleaning or replacement of component parts.

It is another object of the present invention to provide a fluid sampling device which is relatively unbreakable, permits visual inspection of a sample contained therein and which is chemically resistant to the sample.

It is another object of the invention to provide a fluid sampling device having a stopper which is chemically resistant and pliable to provide a reliable seal.

It is a further object of the invention to provide a fluid sampling device which allows for convenient transport of the the sample without the need for separate containers for transport or visual inspection.

It is yet another object of the present invention to provide a fluid sampling device which seals the fluid sample within the device.

To provide a fluid sampling device which is easy to manufacture and use, the actuator is simplified. In accordance with the present invention there is provided a fluid sampling device which includes an elongated tube having an upper end and a lower, fluid receiving end with openings in both of the ends. A rod extends within the tube from the upper end to the fluid receiving end. A stopper is connected to the rod at the fluid receiving end of the tube, and an actuator is pivotally connected to the rod at the upper end of the tube to move the stopper into and out of sealing engagement with the fluid receiving end of the tube. The actuator has a flat guiding surface and a cammed guiding surface which ride along the upper end of the tube as the actuator pivots.

In accordance with another aspect of the invention a top stopper is provided below the actuator, at the upper end of the rod. A cam spacer component is located between the actuator and top stopper. Pivoting of the actuator draws the rod and bottom stopper upwardly to seal the bottom of the tube, and subsequently slides the top stopper downwardly along the rod to seal the top of the elongated tube.

To provide a fluid sampling device which allows visual inspection while being chemically resistant and break resistant, polypropylene extruded to a thickness of 0.050 inches ±0.005 inches is utilized for the sampling tube. This thickness of polypropylene is thin enough to allow visual inspection, yet strong enough to provide a rigid sampling device. To provide a reliable seal, the stopper is formed of neoprene to provide sufficient pliability and coated with polytetrafluoroethylene to provide excellent chemical resistance.

In accordance with another aspect of the invention, various components of the fluid sampler are easily separable and adapted for easy attachment of extension devices to obtain samples from containers of various sizes. The ease of disassembly also simplifies cleaning.

To allow the fluid sampling device to adapt to different types of containers, attachments are made to the basic device. In accordance with another aspect of the present invention there is provided a fluid sampling device which includes an elongated tube having an upper end and a lower end. An elongated attachment tube having an attachment end and a lower, fluid receiving end is connectable to the lower end of the first mentioned tube at the attachment end of the attachment tube. A rod having an upper end and a lower end extends within the first-mentioned tube from the upper end to the lower end of the tube. An attachment rod having an attachment end and a lower, fluid receiving end extends within the attachment tube from the attachment end to the fluid receiving end. The attachment end of the rod is connectable to the lower end of the first-mentioned rod. A stopper is connected to the fluid receiving end of the attachment rod, and an actuator is pivotally connected to the upper end of said first-mentioned rod. The actuator has a flat guiding surface and a cammed guiding surface which ride along the upper end of the tube as the actuator pivots to move the stopper into and out of sealing engagement with the fluid receiving end of the attachment tube.

BRIEF DESCRIPTION OF THE DRAWINGS

Other objects and advantages of the invention will become apparent upon reading the following detail description and upon reference to the drawings in which.

Figure 1:
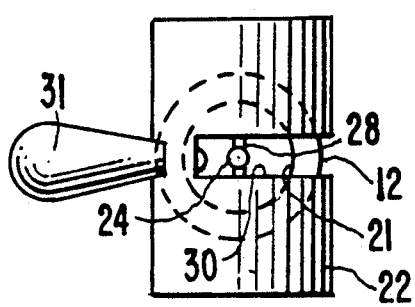
FIG. 1 is a top plan view of a device for obtaining a fluid sample in accordance with the present invention.

While the invention is susceptible to various modifications and alternative forms, specific embodiments thereof have been shown by way of example in the drawings and will be described in detail herein. It should be understood, however, that it is not intended to limit the invention to the particular forms disclosed but on the contrary, the intention is to cover all modifications, equivalents, and alternatives falling within the spirit and scope of the invention as defined by the appended claims.

DESCRIPTION OF THE PREFERRED EMBODIMENT

Figure 2:
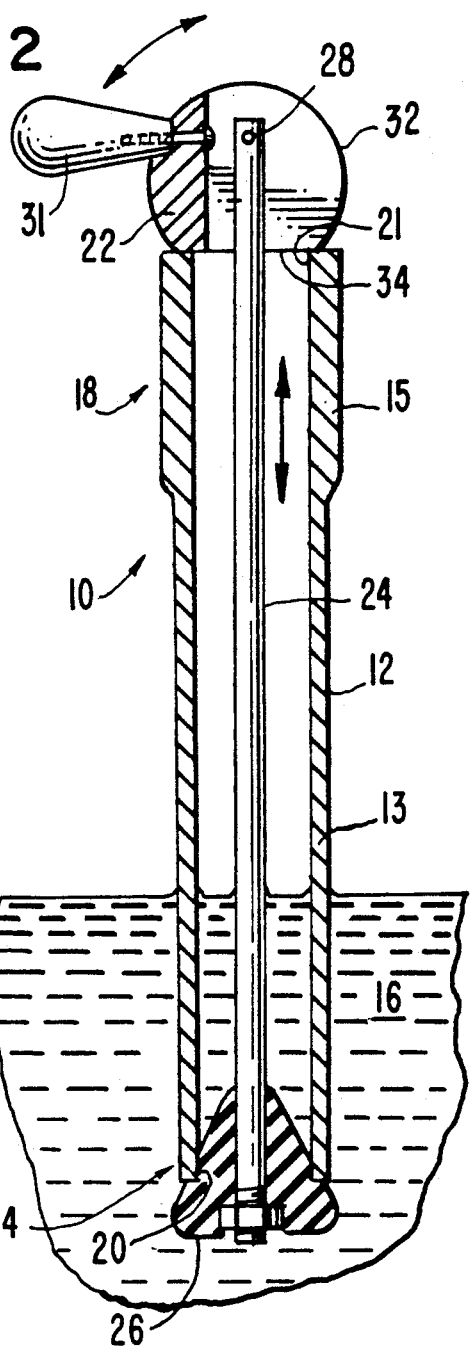
FIG. 2 is a sectional side view of the device of FIG. 1.

Referring to the drawings, wherein a fluid sampling device 10 is shown in FIGS. 1 and 2. A tube 12 has a fluid receiving end 14, which is adapted to be inserted into a fluid medium 16. The upper end 18 of the tube 12 is held above the fluid receiving end 14 to allow fluid to enter the tube 12 through an opening 20 in the fluid receiving end 14.

The technique used for fluid entry is similar to placing a drinking straw into a glass of water. Both ends 14, 18 of the tube 12 contain at least one opening 20,21. As the fluid receiving end 14 of the tube 12 penetrates beneath the surface of the fluid 16, the pressure of the fluid 16, which is greater than the ambient atmospheric pressure, forces fluid 16 into the fluid receiving end 14 of the tube 12. As the fluid 16 enters the tube 12, the air in the tube 12 is forced through the opening 21 in the upper end 18 of the tube 12.

The present invention includes the discovery that by structural modification, polyolefins previously considered unsuitable for sampler construction, could be used to form the tube 12. It was found that a polyolefin tube could be formed to a specific wall thickness range to provide a window within which the translucent material will permit visual inspection of the tube contents while providing the strong, rigid, unbreakable tube having the chemical resistance necessary for universal sampling.

In accordance with an important aspect of the invention, the tube 12 is formed of polypropylene extruded to a thickness of 0.050 inches ±0.005 inches in the fluid receiving portion 13 of the tube. The upper portion 15 of the tube may be thicker in cross-section than the portion 13, or alternatively, the complete tube may be formed to be within the thickness range of 0.050 inches to 0.005 inches. It has been found that polypropylene of this thickness is rigid yet transparent enough to allow for visual inspection of the sample. The use of polypropylene overcomes problems with materials used in prior art devices such as glass, which is easily breakable and clear PVC, which has poor chemical resistance to petroleum-type solvents. Thus, the use of polypropylene having a thickness of 0.050 inches ±0.005 inches solves the material problems of prior art devices while maintaining low cost.

To seal the fluid receiving end 14 of the tube 12 after fluid has entered the tube 12, an actuator 22 and rod assembly 24 bring a stopper 26 into contact with the fluid receiving end 14. Preferably, the stopper 26 is larger in diameter than the fluid receiving end 14 of the tube 12 to provide a leakproof seal. The stopper 26 may be made of a variety of materials, but is preferably made of a resilient material which cannot be damaged by the fluid medium 16. In accordance with an aspect of the invention, it has been found that a neoprene stopper coated with polytetrafluoroethylene solves the problem in providing a stopper which is both chemically resistant and pliable to provide a reliable seal. The actuator 22 is connected to the rod 24 by a pivot pin 28 which extends through the rod 24 in a direction perpendicular to the axial direction, i.e. the direction of motion of the rod 24. To allow the rod 24 to pivot relative to the actuator 22, the rod 24 moves within a slot 30 in the actuator 22. As the actuator 22 is rotated by the handle 31 about the axis of the pivot pin 28, the rod 24 rides within the slot 30. As shown in FIG. 2, the slot 30 provides an opening 21 through which air within the tube 12 is forced as fluid enters the tube 12.

The periphery of the actuator 22 defines a cammed guiding surface 32, and a flat guiding surface 34. The guiding surfaces 32, 34 ride on the upper end 18 of the tube 12. As shown in FIG. 1, the pin 28 is offset from the center of the actuator 22. When the device 10 is placed in a fluid 16, the actuator 22 is pivoted about the pin 28 on the cammed surface 32 so that the stopper 26 is moved away from the opening 20 of the fluid receiving end 14 of the tube 12. After the fluid sample has entered the tube 12, the actuator 22 is pivoted in the opposite direction to capture the fluid sample. When the flat guiding surface 34 is against the upper end 18 of the tube 12, the pin 28 pulls the stopper 26 into engagement with the fluid receiving end 14 of the tube 12 to close the opening 20.

Preferably pin 28 is removably mounted so that after a sample is obtained, the actuator can be removed for use with other sampling tubes. The flat guiding surface 34 provides a stable position for the actuator 22 so that the stopper 26 remains in the closed position to prevent spillage. Alternatively, the pivot pin 28 can be located in the center of the actuator 22, with the cammed guiding surface 32 radially spaced further from the pivot pin 28 than the flat guiding surface 34. The rod 24 is slightly longer than the tube 12, so that the flat guiding surface 34 positions the stopper 26 in an open position away from the fluid receiving end 14 of the tube. As the actuator 22 is rotated, the cammed guiding surface 32 positions the stopper 26 in a closed position in sealing engagement with the fluid receiving end 14 of the tube 12, as the actuator 22 pulls the rod 24 up. When the stopper 26 is in sealing engagement with the fluid receiving end 14 of the tube 12, the device 10 is removed from the fluid medium 16. The tube 12 contains a sample of the fluid 16 which may be transported to a testing device, not shown, for evaluation.

Figure 3:
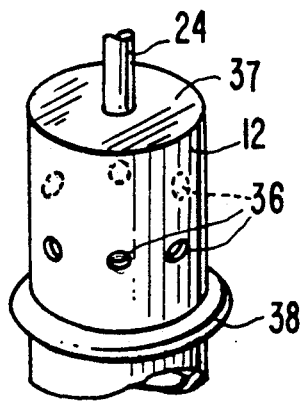
FIG. 3 is a perspective view of the upper end of another embodiment of a device for obtaining a fluid sample in accordance with the present invention.
Figure 5:
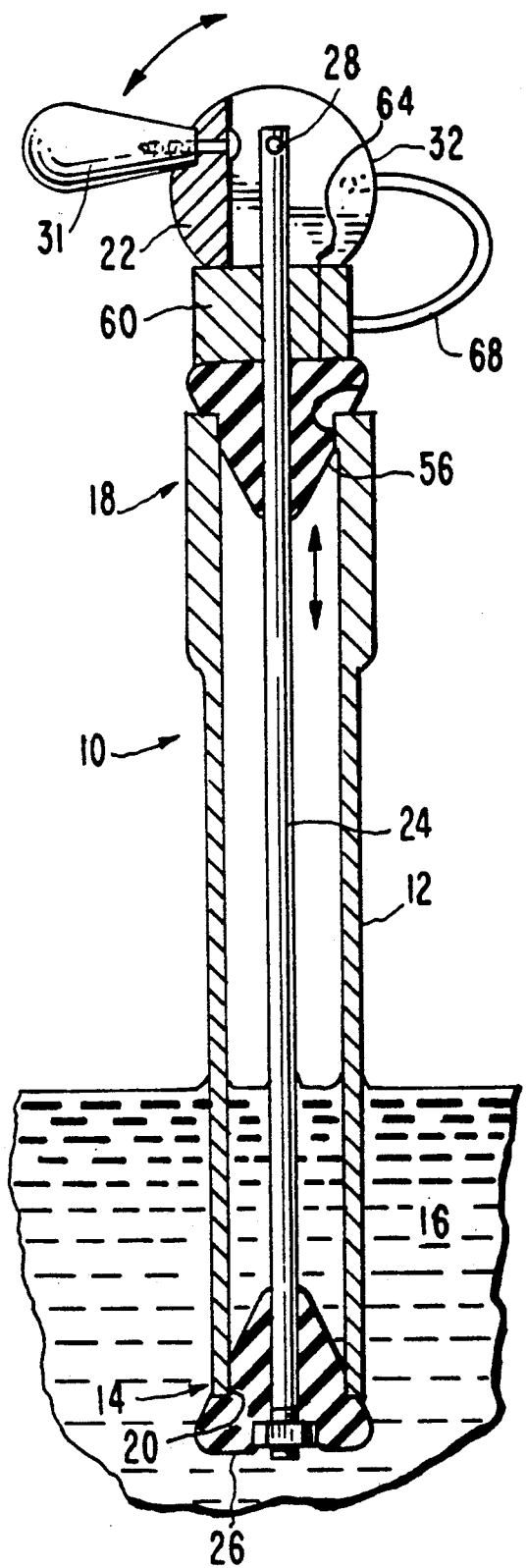
FIG. 5 is a sectional side view of a two stopper device for obtaining a fluid sample in accordance with the present invention.

For particularly hazardous fluids, the upper end 18 of the tube 12 is closed except for a hole large enough to accept the rod 24, as shown in FIG. 3. Preferably a membrane 37 surrounds the hole to provide a fluid tight seal. To allow fluid 16 to enter the tube 12 in this case, one or more holes 36 are formed around the upper end 18 of the tube 12. The holes 36 allow air within the tube 12 to escape when fluid enters the fluid receiving end 14 of the tube 12. After the stopper 26 seals the fluid receiving end 14, a slidable ring 38 is placed over the holes 36 to completely seal the tube 12. Preferably, the membrane 37 and the ring 38 are made of a flexible material which cannot be damaged by the fluid medium.

Where it is desired to seal the tube at both ends, a double stopper arrangement can be utilized, and as shown in FIG. 5, a second conical stopper 56 is provided at the upper end of rod 58. The stopper 56 is tightly secured upon the rod, but slidable upon the application of sufficient force. The actuator 22 as described in conjuction with FIGS. 1 and 2 is also utilized, however, an additional, cam spacer component 60 is positioned between the stopper 56 and actuator 22. The cam spacer component is substantially cylindrical, having a circular face 62 of substantially the same size as the upper face 64 of the conical stopper 56 to apply an even force to the top surface of the pliable stopper 56 to slide the stopper over rod 24.

In operation, with the stoppers 26 and 56 spaced from the ends of the tube 12 and after a sample is received in the tube, the actuator 22 is rotated, causing the cam guiding surface 32 and cam spacer 60 to apply a force upon the stopper 56. As a result, the rod 24 slides upwardly through the stopper 56 until the stopper 26 is seated on the lower end of the tube. Now, continued rotation of the actuator 22 to seat the flat guiding surface 34 on the cam spacer causes the stopper 56 to move downwardly along the rod 24 and seal the upper end of the tube 12.

Figure 8:
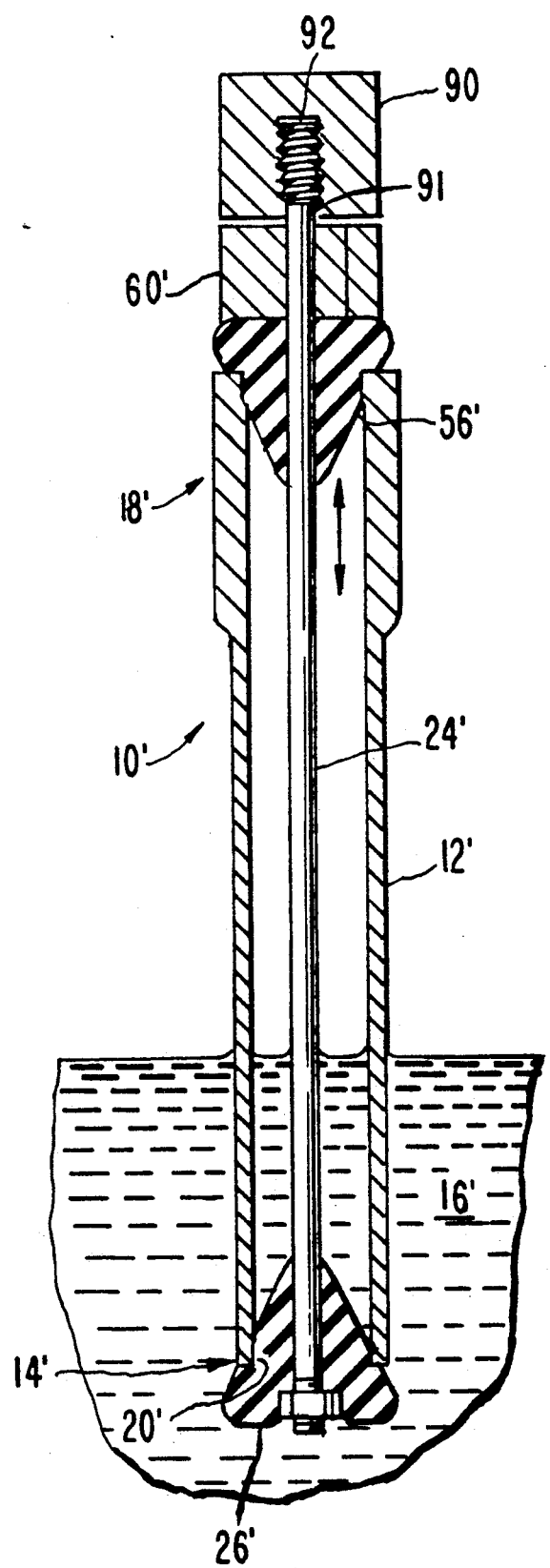
FIG. 8 illustrates a second embodiment of the two stopper arrangement of FIG. 5.

FIG. 8 illustrates a cross-sectional view of a second two stopper embodiment in which a screw cap actuator 90 is utilized for applying force upon cam spacer 60'. In this embodiment, rod 24' is provided with a threaded top portion 92 upon which cap 90 (having corresponding mating threads 91) is rotated, in effect shortening the length of the rod 24'. As in the FIG. 5 embodiment, the actuator 90 applies a force upon a cam spacer 60' which in turn causes stopper 56' to slide upon the rod 24', and place both stoppers in sealing engagement with the tube 12'.

Figure 6:
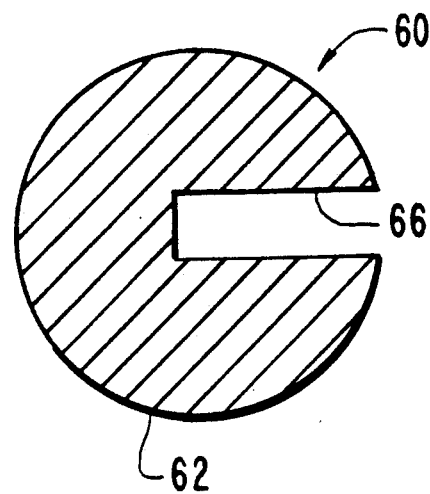
FIG. 6 is a top plan view of the cam spacer of the device shown in FIG. 5.

As shown in FIG. 6, the cam spacer component 60 preferably includes a slot 66 to allow the cam spacer to be readily removed from rod 24 and to allow movement of the rod for sealing/unsealing of the tube. As discussed in conjunction with FIGS. 1 and 2, the actuator 22 is also removably mounted via pin 28. The actuator and cam spacer may thus be removed for use with other sampling tubes. Preferably a nylon cord 68, or other suitable attachment connects the cam spacer and actuator to avoid dropping or loss of the cam spacer from the actuator. The stoppered tube provides a convenient, inexpensive storage/transport device, eliminating the need for separate jars or other storage containers.

As is apparent, the rod 24 for the two stopper arrangement must be longer than the rod required for a single stopper, to accommodate the additional stopper and the cam spacer 60. This may be accomplished using a longer one-piece rod, or using a threaded rod extension as discussed in connection with FIG. 4.

The ease of disassembly of the device also provides for easy cleaning. For example, after the rod 24, or 50 is removed from the tube, the tube can be easily cleaned using a tube brush or squeegee device. This avoids the possibility that remnants of a sample will contaminate subsequent samples. For highly contaminated samples, the acutator 22 and cam spacer 60 can be removed and the sealed tube can be discarded.

Figure 4:
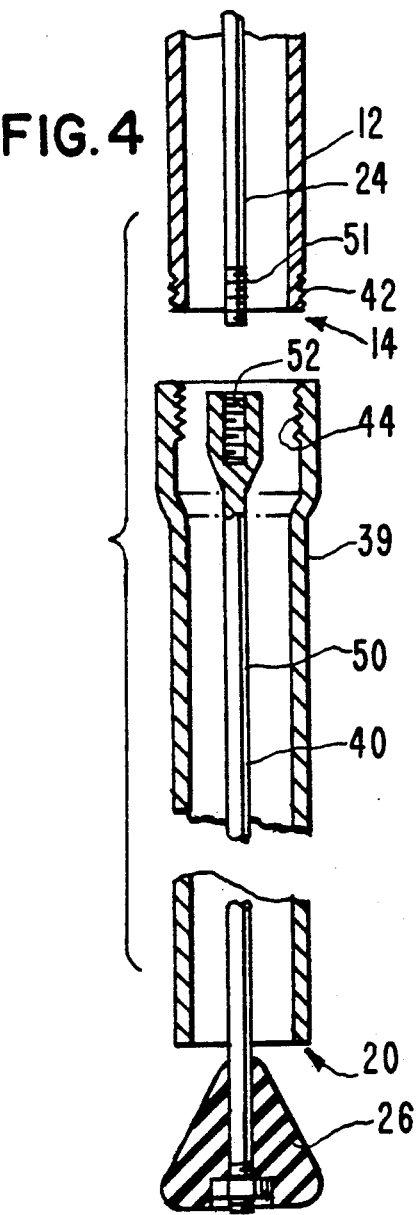
FIG. 4 illustrates a second embodiment of a device for obtaining a fluid sample in accordance with the present invention.

To sample fluid from a deep reservoir, an additional length of tube 39 and an additional length of rod 40, as shown in FIG. 4, are attached to the device 10. To facilitate this attachment, the fluid receiving end 14 of the tube 12 has outer threads 42 which screw threadably engage with inner threads 44 on the piece of attachment tube 39. Likewise, the stopper 26 is unscrewed from the rod 24, and a length of an attachment rod 50 is screwed onto a threaded portion 51 of the rod 24 via the internal threads 52 of the attachment rod 50. One or more attachment tubes 39 of various lengths are attached to the tube 24 so that samples can be obtained from deep reservoirs. Moreover, attachment tubes 39 having a smaller diameter than the tube 12 are attached so that fluid samples can be obtained from containers having narrow openings.

Figure 7:
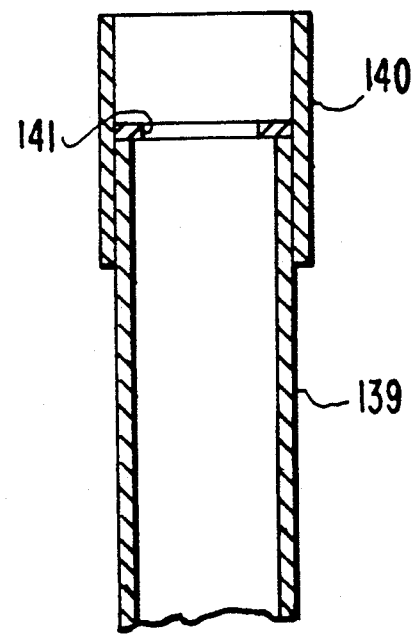
FIG. 7 is a side sectional view of a sampler tube with a tube coupler.

In addition to, or in lieu of the use of threaded tube coupling, sampler tubes may be joined by a tube coupler 140 as shown in FIG. 7. The tube coupler 140 is sized such that a tube 139 can be slidably received within the coupler, tightly enough such that a sample liquid will not leak through the tube coupler. An inwardly protruding annular ring 141 is provided on the tube coupler so that a pair of tubes can be properly positioned within the coupler. The ring 141 also reduces the possibility of leakage. In use, a pair of tubes are slid inside of the coupler 140 until the tube ends abut ring 141. The coupler allows tubes to be joined on site (as where a sample is to be obtained from a deep tank or reservoir), so that numerous different sized tubes are not required.

In addition, with the rod and stopper assembly removed, the tube can be used in obtaining solid or semi-solid samples, for example in obtaining a sludge sample. Using the tube and tube coupler assembly (as shown in FIG. 7) the tube is carved down into the sludge, and then removed which removes a plug of sludge along with any liquid lying atop the sludge. The liquid/sludge sample is then discharged into a container using a suitable sludge plunger.

Other aspects, objects and advantages of this invention can be obtained from a study of the drawings, the disclosure and the appended claims.

We claim:

1. A fluid sampling device comprising:
    an elongated tube having an upper end and a lower, fluid receiving end, said tube having openings in both of said ends, said tube being formed of a polyolefin with a tube wall having at least a section extruded to a thickness of 0.05 inches ±0.005 inches;
    an actuator rod extending within said tube from the upper end to the fluid receiving end;
    a membrane covering the upper end of said elongated tube, said membrane allowing said actuator rod to extend therethrough and providing a fluid tight seal between said tube and said actuator rod, said tube including at least one opening adjacent said upper end;
    means for covering said opening;
    a stopper connected to said rod at the fluid receiving end of said tube; and
    actuator means connected to an upper end of said actuator rod to move said stopper into and out of sealing engagement with the fluid receiving end of said elongated tube such that a liquid sample may be obtained through said fluid receiving end when said stopper is out of sealing engagement, and the sample is retained in said elongated tube by movement of said stopper into sealing engagement with the fluid receiving end of the tube, whereby the sample may be visually inspected through the polyolefin tube.

2. The fluid sampling device of claim 1, wherein said stopper is formed of neoprene coated with polytetrafluoroethylene.

3. The fluid sampling device of claim 1 wherein said actuator means is pivotally connected to the upper end of said rod and includes a flat surface and a cammed guiding surface which ride along the upper end of said elongated tube as the actuator means pivots to move the stopper into and out of engagement with the fluid receiving end of said elongated tube.

4. A fluid sampling device for insertion into a fluid for purposes of obtaining a fluid sample comprising:
    an elongated tube having a sidewall, an upper end and a lower, fluid receiving end, said tube having openings in both of said ends and being extruded from translucent polypropylene with at least a section of said sidewall being extruded to a thickness of 0.050 inches ±0.005 inches to render said section more transparent to permit inspection of the tube contents;
    an actuator rod extending within said tube from the upper end to the fluid receiving end, said actuator rod being formed to extend outwardly through the opening in said upper end of said tube and being movable relative to said tube toward and away from the lower fluid receiving end thereof;
    a first stopper connected to said actuator rod at the fluid receiving end of said tube and fixed relative thereto, said first stopper being dimensioned to close the fluid receiving end of the tube when the first stopper is moved to a closure position where the first stopper is in sealing engagement with the fluid receiving end of the tube;
    a second stopper mounted on said actuator rod for sliding movement relative thereto, said second stopper being positioned at the upper end of said tube for closing the opening in said upper end;

actuator means connected to said actuator rod externally of said tube adjacent to the upper end thereof and operative to cause said actuator rod to move said first stopper between an open position where fluid is permitted to enter the fluid receiving end of said tube and air is permitted to exit the upper end of said tube at the closure position whereby a fluid sample is obtained, said actuator means including an actuation unit having a flat guiding surface, a cammed guiding surface, a slot formed therein substantially perpendicular to said flat guiding surface to receive said actuator rod, and a pivot pin means mounted within said slot and extending through said actuator rod and into said actuating unit on either side of said actuator rod, said pivot pin means extending substantially perpendicular to said actuator rod permitting said actuating unit to pivot between a first position where said flat guiding surface is adjacent to the second stopper to a second position where said cammed guiding surface is adjacent to the second stopper;

said actuator means operating during a single actuation to move said first stopper from a position externally of said tube to a closure position against the end of said tube and to subsequently seal said first and second stoppers against the ends of said tube.

5. The fluid sampling device of claim 4 wherein said pivot pin means is removable to permit said actuating unit to be removed from said actuator rod.

6. The fluid sampling device of claim 4 wherein both said first and second stoppers are positioned by said actuator rod externally of said tube and are moved by said actuator means into the open ends of said tube, said actuator means including a cam spacer separate from said actuating unit and positioned between said actuating unit and said second stopper, said cam spacer having a lower surface for contacting said second stopper and an upper surface for contact with said actuating unit, said actuator rod extending through said second stopper and cam spacer to said actuating unit and being slidable relative to said cam spacer.

7. The fluid sampling device of claim 6 wherein said first and second stoppers are formed of neoprene coated with polytetrafluoroethylene.

8. The fluid sampling device of claim 6 wherein said cam spacer is removable from said actuator rod.

9. The fluid sampling device of claim 8 wherein said cam spacer includes an open ended slot to receive said actuator rod.

10. The fluid sampling device of claim 9 wherein said actuating unit pivots about said pivot pin between a first position where said flat guiding surface is in contact with the upper surface of said cam spacer and a second position where said cammed guiding surface is in contact with the upper surface of said cam spacer.

11. The fluid sampling device of claim 10 wherein said stoppers are formed of neoprene coated with polytetrafluoroethylene.

12. The fluid sampling device of claim 4 wherein the section of said sidewall extruded to a thickness of 0.050 inches ±0.005 inches constitutes a first section extending upwardly from the lower, fluid receiving end of said tube, said sidewall including a second section extending from said first section to the upper end of said tube, said second section being translucent and of a greater thickness than said first section.

13. A fluid sampling device comprising:

an elongated tube having an upper end and a lower fluid receiving end, said tube having a sidewall extending between said upper and lower ends and an opening formed in each of said ends, said sidewall being extruded from translucent polypropylene with at least a section of said sidewall being extruded to a thickness of 0.050 inches ±0.005 inches to render said section more transparent to permit visual inspection of the tube contents;

an actuator rod extending within said tube from the upper end to the fluid receiving end, said actuator rod being of a length greater than the length of said tube and formed to extend through the opening in said upper end of the tube;

a first stopper secured to the actuator rod at the fluid receiving end of the tube and being dimensioned to close the fluid receiving end of the tube when the first stopper is moved to a closure position where the first stopper is in sealing engagement with the fluid receiving end of the tube, said first stopper being fixed in non-sliding relationship on said actuator rod;

a second stopper mounted on said actuator rod for sliding movement relative thereto, said second stopper being positioned at the upper end of said tube for closing the opening in said upper end, both said first and second stoppers being positioned by said actuator rod externally of said tube;

actuator means connected to said actuator rod externally of said tube adjacent to the upper end thereof and operative in a single actuation operation to cause relative sliding movement between said actuator rod and said second stopper to move said first stopper between an open position where fluid is permitted to enter the fluid receiving end of said tube and air is permitted to pass through the upper open end of said tube to a position in engagement with the fluid receiving end of said tube and to subsequently cause continued relative sliding movement between said actuator rod and said second stopper to bring said first and second stoppers into sealing engagement with the lower and upper ends of said tube respectively, said actuator means including an actuating unit removably mounted at the end of said actuator rod and a cam spacer positioned between said actuating unit and said second stopper, said cam spacer having a lower surface for contacting said second stopper and an upper surface for contact with said actuating unit, said actuator rod extending through said cam spacer to said actuating unit and being slidable relative to said cam spacer.

14. The fluid sampling device of claim 13 wherein said cam spacer and actuating unit are removable from said actuating rod.

15. The fluid sampling device of claim 14 wherein said cam spacer includes an open ended slot to receive said actuator rod.

16. The fluid sampling device of claim 15 wherein an end section of said actuator rod extending externally at the upper end of said tube is threaded, said actuating unit including a threaded central opening engaging the threaded end section of said actuator rod.

17. A fluid sampling device for insertion into a fluid for purposes of obtaining a fluid sample comprising:

an elongated tube having a sidewall, an upper end and a lower, fluid receiving end, said tube having opposed openings in both of said ends, with the opening of said upper end being smaller in diameter than the opening at said lower end, an actuator rod extending within said tube from the upper end to the fluid receiving end, said actuator rod being formed to extend through the opening in said upper end of said tube and to fill said opening while being slidable within said opening, at least one side opening formed in the sidewall of said tube at the upper end thereof, closure means mounted upon said sidewall for selectively opening or closing said side opening, said closure means including a sealing ring slidably mounted on said sidewall, a stopper connected to said actuator rod at the fluid receiving end of said tube, said stopper being dimensioned to close the fluid receiving end of the tube when the stopper is moved to a closure position where the stopper is in sealing engagement with the fluid receiving end of the tube, and actuator means connected to said actuator rod externally of said tube adjacent to the upper end thereof and operative to cause said actuator rod to move said stopper between an open position where fluid is permitted to enter the fluid receiving end of said tube to the closure position whereby a fluid sample is obtained, said actuator means including an actuator member contacting the upper end of said tube, said actuator member having a flat guiding surface and a cammed guiding surface for contacting the upper end of said tube and a slot formed therein to receive said actuator rod, and a pivot pin means mounted within said slot and extending through said actuator rod and into said actuator member on either side of said actuator rod, said pivot pin means extending substantially perpendicular to said actuator rod permitting said actuator member to pivot between a first position where said flat guiding surface is in contact with the upper end of said tube to a second position where said cammed guiding surface is in contact with the upper end of said tube.

18. The fluid sampling device as set forth in claim 17 wherein said slot extends substantially perpendicular to said flat surface.

19. The fluid sampling device as set forth in claim 18, wherein said pin means is offset from the center of said actuator member.

20. The fluid sampling device, as set forth in claim 19, wherein said stopper in the closed position seals the opening in the fluid receiving end of said tube when said flat guiding surface is in contact with the upper end of said tube.

21. The fluid sampling device, as set forth in claim 19, wherein said stopper in the open position extends below the fluid receiving end of said tube when said cammed guiding surface is in contact with the upper end of said tube.

22. The fluid sampling device as set forth in claim 21, wherein said stopper in the closed position seals the opening in the fluid receiving end of said tube when said flat guiding surface is in contact with the upper end of said tube.

23. The fluid sampling device as set forth in claim 17 wherein said elongated tube includes an upper section including said tube upper end and a lower section including said tube fluid receiving end, each said upper section and lower section having an attachment end and connector means formed on said attachment ends to removably connect said lower section to said upper section;

said rod including an upper rod section connected to said actuator means and a lower rod section connected to said stopper, each said upper rod section and lower rod section having a rod attachment end and rod connection means formed on said rod attachment ends to removably connect said lower rod section to said upper rod section.

24. The fluid sampling device of claim 17 wherein said elongated tube is formed of polypropylene extruded to a thickness of 0.050 inches ±0.005 inches.

* * * * *